United States Patent
Hollenbeck

(10) Patent No.: US 6,294,205 B1
(45) Date of Patent: Sep. 25, 2001

(54) BOTANICAL COMPOSITION FOR SOOTHING SKIN

(76) Inventor: Brenda Jean Hollenbeck, 513 Suncreek Trail, Redding, CA (US) 96003

( * ) Notice: Subject to any disclaimer, the term of this patent is extended or adjusted under 35 U.S.C. 154(b) by 0 days.

(21) Appl. No.: 09/450,874

(22) Filed: Nov. 29, 1999

(51) Int. Cl.[7] .................................................. A61K 35/78
(52) U.S. Cl. .................... 424/736; 424/401; 514/861; 514/862; 514/863; 514/864; 514/865; 514/887
(58) Field of Search ................. 424/175.1, 401, 424/736; 514/861–865, 887

(56) References Cited

U.S. PATENT DOCUMENTS

| | | |
|---|---|---|
| 3,830,913 | 8/1974 | Harich . |
| 5,378,465 * | 1/1995 | Zeines ............................... 424/195.1 |
| 5,407,663 * | 4/1995 | Eisen ....................................... 424/49 |
| 5,425,944 | 6/1995 | Harich . |
| 5,631,004 * | 5/1997 | Harich et al. ........................... 424/58 |
| 5,723,106 * | 3/1998 | Buch et al. ............................. 424/49 |
| 5,772,986 * | 6/1998 | Kross ...................................... 424/53 |
| 5,814,031 | 9/1998 | Mooney et al. . |
| 5,916,573 | 6/1999 | Spiers et al. . |

* cited by examiner

Primary Examiner—Christopher R. Tate

(57) ABSTRACT

A botanical composition for soothing irritated skin and method of producing the composition. The composition includes 90–97% by weight aloe juice; 1–5% by weight grapefruit seed and pulp extract; and 1–5% by weight vegetable glycerine. The aloe juice, grapefruit seed and pulp extract and vegetable glycerine are mixed together to form a liquid mixture for application to and covering the irritated skin. The grapefruit seed and pulp extract preferably has a pH of 3. A fragrance may be added to the composition to provide a desired odor to the composition and oils may be added to the composition for use in hydrating the irritated skin on which the composition is applied. The composition is stored in a spray bottle for creating a mist of the composition when applying the composition to the irritated skin.

10 Claims, 2 Drawing Sheets

BOTANICAL COMPOSITION FOR SOOTHING SKIN

BACKGROUND OF THE INVENTION

1. Field of the Invention

Figure 1:
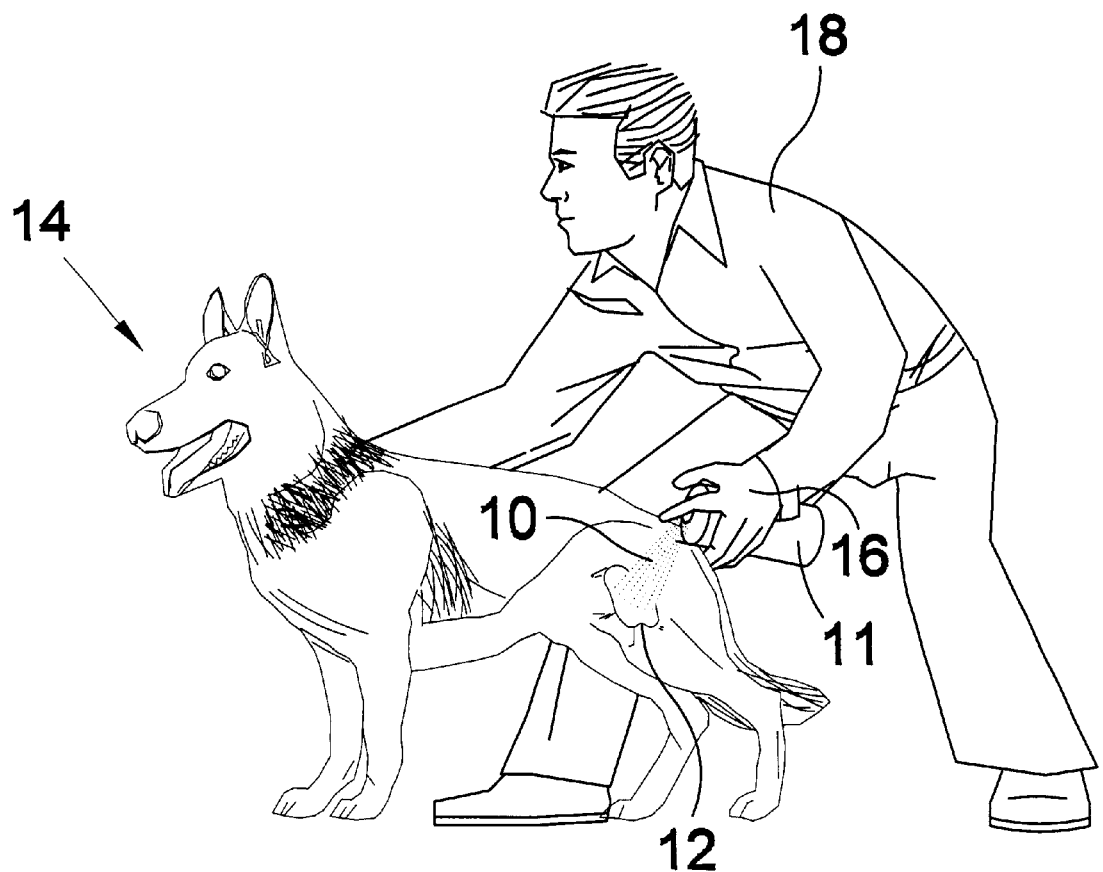

The present invention relates generally to botanical compositions and, more specifically, to a botanical composition able to soothe the skin of dogs infected with "hotspots" and soothe the skin of humans irritated by eczema and/or psoriasis.

2. Description of the Prior Art

Numerous types of mixtures for soothing the skin have been provided in the prior art. For example, U.S. Pat. Nos. 3,830,913; 5,425,944; 5,814,031 and 5,916,573 all are illustrative of such prior art. While these units may be suitable for the particular purpose to which they address, they would not be as suitable for the purposes of the present invention as heretofore described.

U.S. Pat. No. 3,830,913

Inventor: Jakob Harich

Issued: Aug. 20, 1974

A composition effective as a biocidal agent is prepared by adding 2-phenoxy-ethanol to a grapefruit derivative prepared by reacting the pulps of fresh grapefruit with an organic alcohol or keystone in the presence of a free radical initiator and then successively adding n-alkyl substituted dimethyl benzyl ammonium chloride, isopropyl alcohol, and 1-(3-chloroallyl)-3,5,7-triaza-1-azonia-adamantane chloride. The filan composition is effective against a broad spectrum of gram positive and gram negative microorganisms.

U.S. Pat. No. 5,425,944

Inventor: Jakob Harich

Issued: Jun. 20, 1995

A ground mixture (80:20 by weight) of dried grapefruit seeds and grapefruit pulp respectively is subjected to extraction using an equal amount by weight of glycerin. The resulting extract is an effective bactericide, fungicide, and virucide, and is expected to be particularly effective in the treatment of HIV infections.

U.S. Pat. No. 5,814,031

Inventor: Mark Mooney et al.

Issued: Sep. 29, 1998

This invention relates to a composition containing a hydrophobic solvent, a network polymer and a flow control agent which is useful in healing wounds. The composition of this invention may be applied directly to a wound to create a structured occlusive dressing. The dressings of this invention do not migrate, but maintain their integrity at skin temperature, and encourage the creation of a moist wound environment while protecting the wound in order to accelerate healing.

U.S. Pat. No. 5,916,573

Inventor: Samantha M. Spiers et al.

Issued: Jun. 29, 1999

A grape seed oil composition for topical application to the skin comprising: a) about 1 to about 99% by weight of grape seed oil; b) at least one hydrating agent; and c) water. Hydrating agents include vegetable glycerin, aloe-vera, and vegetable oils other than grapeseed oil, for example, vitamin E oil, jojoba oil, flaxseed oil, primrose oil and any other botanical oil. The grapeseed oil composition may further include at least one amino acid, for example, lysine and tyrosine.

SUMMARY OF THE PRESENT INVENTION

The present invention relates generally to botanical compositions and, more specifically, to a botanical composition able to soothe the skin of dogs infected with "hotspots" and soothe the skin of humans irritated by eczema and/or psoriasis.

A primary object of the present invention is to provide a botanical composition for soothing skin that will overcome the shortcomings of prior art devices.

A further object of the present invention is to provide a botanical composition for soothing skin which is able to soothe the pain and discomfort associated with hotspots, e.g. lick granuloma, on dogs.

A yet further object of the present invention is to provide a botanical composition for soothing skin which is able to soothe the pain and discomfort associated with eczma and psoriasis on humans.

Another object of the present invention is to provide a botanical composition for soothing skin which is able to be easily applied to the affected area.

A still further object of the present invention is to provide a botanical composition for soothing skin which is in liquid form and able to be sprayed on the affected area.

A further object of the present invention is to provide a botanical composition for soothing skin including all natural elements combined in a mixture.

A further object of the present invention is to provide a botanical composition for soothing skin having a bitter taste to prevent animals from licking the composition off the affected area.

Another object of the present invention is to provide a botanical composition for soothing skin that is simple and easy to use.

A still further object of the present invention is to provide a botanical composition for soothing skin that is economical in cost to manufacture.

Additional objects of the present invention will appear as the description proceeds.

A botanical composition for soothing irritated skin and method of producing the composition. The composition includes 90–97% by weight aloe juice; 1–5% by weight grapefruit seed and pulp extract; and 1–5% by weight vegetable glycerine. The aloe juice, grapefruit seed and pulp extract and vegetable glycerine are mixed together to form a liquid mixture for application to and covering the irritated skin. The grapefruit seed and pulp extract preferably has a pH of 3. A fragrance may be added to the composition to provide a desired odor to the composition and oils may be added to the composition for use in hydrating the irritated skin on which the composition is applied. The composition is stored in a spray bottle for creating a mist of the composition when applying the composition to the irritated skin.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

Figure 2:
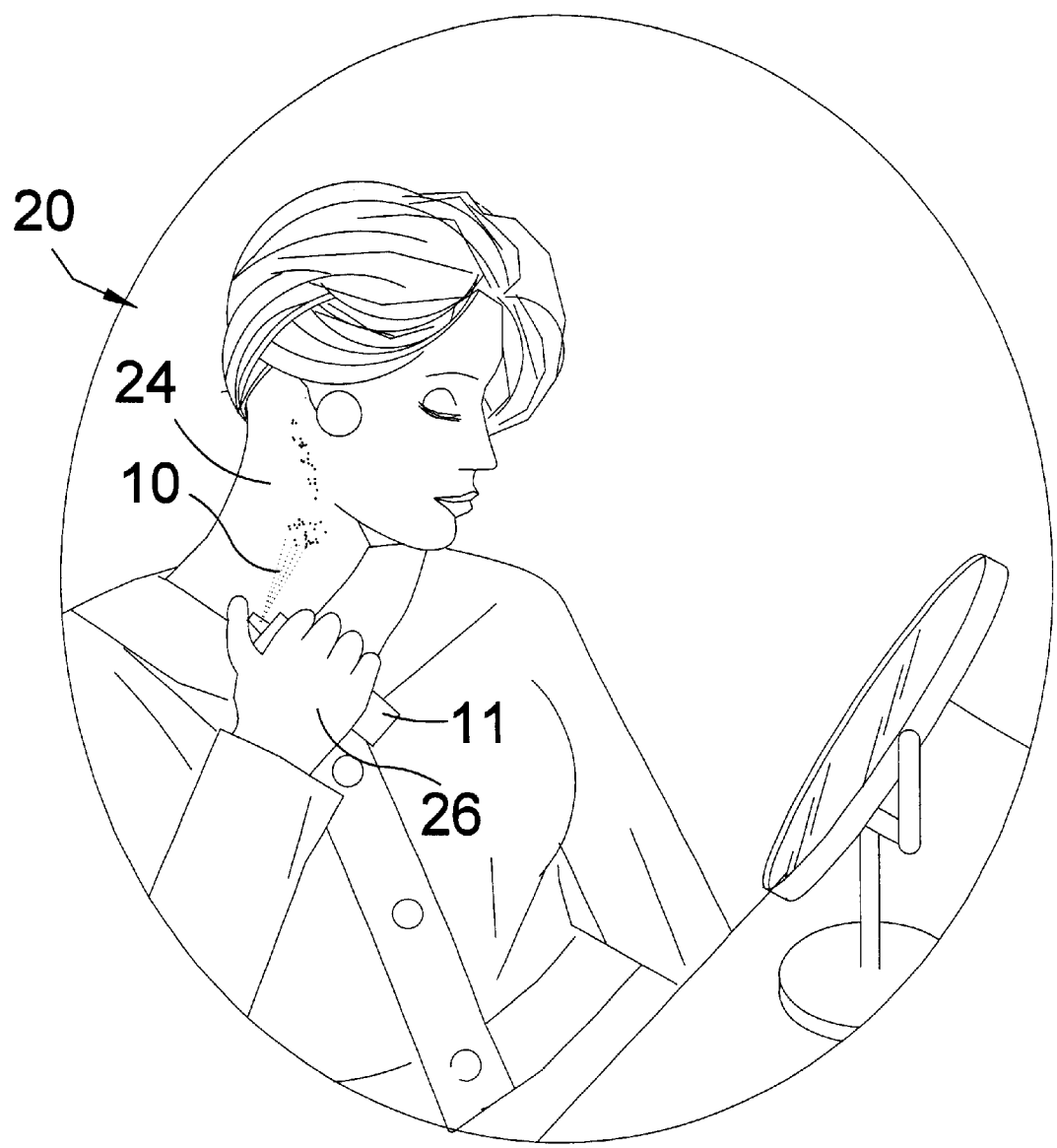

FIG. 1 is a perspective view of the botanical composition for soothing skin of the present invention being applied to the skin of a dog to soothe the discomfort associated with hotspots; and FIG. 2 is a perspective view of the botanical composition for soothing skin of the present invention being applied to eczema on a person to soothe the discomfort associated with the skin condition.

DESCRIPTION OF THE REFERENCED NUMERALS

Turning now descriptively to the drawings, in which similar reference characters denote similar elements throughout the several views, the Figures illustrate the botanical composition for soothing skin of the present invention. With regard to the reference numerals used, the following numbering is used throughout the various drawing figures.

- 10 botanical composition for soothing skin of the present invention
- 11 spray bottle holding botanical composition for soothing skin therein
- 12 hotspots
- 14 dog
- 16 hand activating spray bottle for applying botanical composition
- 18 person traeting dog
- 20 person suffering from eczema
- 22 skin of person
- 24 eczema on skin of person
- 26 hand activating spray bottle

DETAILED DESCRIPTION OF THE PREFERRED EMBODIMENT

Turning now descriptively to the drawings, in which similar reference characters denote similar elements throughout the several views, FIGS. 1 and 2 illustrate the botanical composition for soothing skin of the present invention indicated generally by the numeral 10.

The botanical composition for soothing skin 10 is shown in FIG. 1 being applied to a "hotspot" 12 on a dog 14. The botanical composition for soothing skin 10 is in liquid form and contained in a spray bottle 11 and is used to soothe skin which is irritated by "hotspots" 12 and the sensitive area surrounding the "hotspots" on a dog 14. "Hot spots" 12, e.g. lick granuloma, are a normal skin irritation which affects dogs 14 and cats. When a dog or cat is affected by this condition, lesions usually form on the skin and are very uncomfortable to the animal. The animal also tends to lick the infected area thus further irritating the affected area.

In order to use the botanical composition for soothing skin 10 to relieve the irritation, the spray bottle 11 containing the botanical composition for soothing skin 10 is grasped in a hand 16 of a person 18 and pointed at the affected area. When the spary bottle 11 is activated, a mist of the botanical composition for soothing skin 10 is caused to exit the bottle 11 and be applied to the affected area of skin until completely coated. The botanical composition for soothing skin 10 is bitter in taste to dissuade the animal to which it is applied from licking the affected and covered area. As the animal is dissuaded from licking the affected area due to the bitter taste of the botanical composition for soothing skin 10, the area is not further irritated and is able to heal more quickly. Thus, the affected area is soothed by the botanical composition for soothing skin 10 and will not be guarded from further irritation thereby allowing the area to heal more quickly.

Preferably, the botanical composition for soothing skin 10 is applied to the affected area twice a day for between 2–7 days or for as long as relief from the pain and irritation associated with the "hotspots" is soothed. Should no further soothing effect be noticeable for a period of at least two days and the "hotspot" is still present, additional precautions should be taken such as consulting a veterinarian.

The botanical composition for soothing skin 10 is also effective for treating eczema and psoriasis in humans as illustrated in FIG. 2. This figure shows a person 20 applying the botanical composition for soothing skin 10 to an area of skin 22 infected by eczema 24. The spray bottle 11 containing the botanical composition for soothing skin 10 is held in the hand 26 of the person 18 and applied to the area affected by eczema 24 in a manner similar to that described above. The botanical composition for soothing skin 10 is sprayed to cover the area of skin 22 surrounding and infected by the eczema or psoriasis 24 until coated thereby. Preferably, the botanical composition for soothing skin 10 is applied to the affected area twice a day for as long as the soothing effects of the botanical composition for soothing skin 10 are felt. Should the soothing effects not be minimized and the skin condition still be present for at least two days while using the botanical composition for soothing skin 10, use of the botanical composition for soothing skin 10 should be discontinued and a physician should be consulted.

The botanical composition for soothing skin 10 is formed from a combination of Aloe Vera juice, grapefruit seed and pulp extract and vegetable glycerin. The botanical composition for soothing skin 10 preferably contains 90–97 wt % Aloe Verajuice, 1–5 wt. % grapefruit seed and pulp extract and 1–5 wt. % vegetable extract. In order to produce a 128 oz. sample of the botanical composition for soothing skin 10 substantially one gallon (128 fl. oz.) of Aloe Vera juice is mixed with approximately 4 ounces of grapefruit seed and pulp extract. The mixture is then mixed with approximately 4 ounces of vegetable extract. Mixing continues until the botanical composition for soothing skin 10 reaches a desired consistency. Once the elements are thoroughly mixed together, the mixture is allowed to sit for approximately 24 hours. During this time, the mixture will naturally darken to a golden amber color as the ingredients bond together. The mixture is then placed in the spray bottle 11 for use. Prior to each use, the bottle 11 should be shaken to remix the ingredients. Fragrances and oils may also be added to the botanical composition for soothing skin 10 to provide a desired scent to the mixture or to add skin softening qualities to the mixture without effecting the soothing feeling provided by the botanical composition for soothing skin 10. The addition of fragrances to the botanical composition for soothing skin 10 allows any odor associated therewith to be covered up by a desired pleasant smelling odor. This further allows the botanical composition for soothing skin 10 to be produced in numerous different varieties for providing the user with a scent that appeals to them and is pleasant to those around them. The oils which may be added to the botanical composition for soothing skin 10 also do not affect the effectiveness of the mixture for soothing the affected area of the skin.

The grapefruit seed and pulp extract preferably has a pH of 3. Grapefruit seed and pulp extract of such a pH level will make the mixture bitter enough to dissuade animals from licking the area to which the botanical composition for soothing skin 10 is applied. The vegetable glycerine is added tot he mixture to provide body thereto and aid the botanical composition for soothing skin 10 in sticking to the area to which it is applied. Thus, the botanical composition for soothing skin 10 will not run when applied and will remain as a coating for the irritated area of skin.

The aloe juice used in the botanical composition for soothing skin 10 normally contains Sodium Benzoate which acts as a stabilizer. However, aloe juice such as a ½% solution which does not contain Sodium Benzoate may also be used to produce the botanical composition for soothing skin 10.

In experimental applications to "hot spots" occurring on dogs wherein the dog had lost hair covering the affected portion of the body, 98% of all cases have resulted in diminishing the "hot spot" covering the affected area by 50% after application of the botanical composition for soothing skin 10 twice daily for 2 days. Within 4–5 days most instances of "hot spots" treated by the botanical composition for soothing skin 10 were completely healed. The botanical composition for soothing skin 10 was thus able to soothe the skin of the dog while the bitter taste prevents the dog from irritating the affected area. The affected area is thus allowed to heal without further irritation by the dog thereby reducing the required healing time. The botanical composition for soothing skin 10 has also been found to be effective in soothing the skin of humans infected with eczema, dermititis and psoriasis.

The operation of the botanical composition for soothing skin 10 will now be described with reference to the figures. In operation, the botanical composition for soothing skin 10 is prepared by mixing the grapefruit seed and pulp extract with the Aloe Vera juice. The vegetable glycerine is then added in the correct proportions disclosed above. This combination is thoroughly mixed together for a few minutes. At that time any fragrance for odor or oils for hydration of the skin may be added to the botanical composition for soothing skin 10 and mixed in. The mixture is then allowed to sit for substantially 24 hours. The color of the botanical composition for soothing skin 10 darkens as it sits and the elements blend together. The botanical composition for soothing skin 10 is ready for use when the color of the mixture has darkened to a golden amber color. The grapefruit seed and pulp extract is preferably of a pH of 3 which provides a sufficiently bitter taste so that when used on animals, the animal is dissuaded from licking the area to which the botanical composition for soothing skin 10 is applied. The vegetable glycerine provides body to the mixture and allows the botanical composition for soothing skin 10 to stick to the applied area without running off or being easily wiped off.

The botanical composition for soothing skin 10 is a liquid and is placed in a spray bottle for use after it has turned to the golden amber color indicating the mixture is ready for use. In order to use the botanical composition for soothing skin 10, the spray bottle is pointed to an infected area of skin and activated to spray a mist of the botanical composition for soothing skin 10. The botanical composition for soothing skin 10 is thus sprayed on the irritated area and is caused to cover the area. The botanical composition for soothing skin 10 then acts to cover and soothe the area allowing proper time for the area to heal without irritation such as an animal licking the area.

From the above description it can be seen that the botanical composition for soothing skin of the present invention is able to overcome the shortcomings of prior art devices by providing a botanical composition for soothing skin which is able to. Furthermore, the botanical composition for soothing skin of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A botanical composition for soothing irritated skin, said composition whose effective ingredients consist of:
   a) aloe juice within a range of 90–97% by weight of the composition;
   b) grapefruit seed and pulp extract with a pH of about 3 and within a range of between 1–5% by weight of the composition; and c) vegetable glycerine within a range of between 1–5% by weight of the composition, wherein said aloe juice, grapefruit seed and pulp extract and vegetable glycerine are mixed together to form a liquid mixture for application to and covering the irritated skin.

2. The botanical composition for soothing skin as recited in claim 1, further comprising a fragrance added to said composition to provide a desired odor to said composition.

3. The botanical composition for soothing skin as recited in claim 1, further comprising oil added to said composition for use in hydrating the irritated skin on which said composition is applied.

4. The botanical composition for soothing skin as recited in claim 1, wherein said composition is positioned within a spray bottle for creating a mist of said composition when applying said composition to the irritated skin.

5. A method of producing a botanical composition for soothing irritated skin, said method comprising the steps of:
   a) mixing together aloe juice in the amount of between 90–97% by weight of the composition and grapefruit seed and pulp extract in the amount of between 1–5% by weight of the composition;
   b) mixing vegetable glycerine in the amount of between 1–5% by weight of the composition with the aloe juice and grapefruit seed and pulp extract to form a liquid;
   c) allowing the mixture to sit for about 24 hours until turning a golden amber color; and
   d) placing the mixture in a spray bottle for use.

6. The method as recited in claim 5, further comprising the step of placing the composition in a spray bottle for generating a mist of the composition when the spray bottle is activated activated.

7. The method as recited in claim 6, wherein said grapefruit seed and pulp extract has a pH of 3.

8. The method as recited in claim 5, further comprising the step of adding a fragrance added to said composition to provide a desired odor to said composition.

9. The method as recited in claim 5, further comprising the step of adding oil added to said composition for use in hydrating the irritated skin on which said composition is applied.

10. The method of soothing the irritated skin of a dog or a cat comprising:
   a) spraying the liquid botanical composition according to claim 1 on the irritated area of the skin until the affected area is completely coated; and
   c) repeating the application twice a day for between 2 and 7 days.

\* \* \* \* \*